(12) United States Patent
Miles et al.

(10) Patent No.: US 10,723,902 B2
(45) Date of Patent: Jul. 28, 2020

(54) CONDUCTIVE INK

(71) Applicant: DST Innovations Limited, Bridgend (GB)

(72) Inventors: Anthony Miles, Bridgend (GB); Benjamin John Masheder, Portishead (GB)

(73) Assignee: DST Innovations Limited, Bridgend (GB)

( * ) Notice: Subject to any disclaimer, the term of this patent is extended or adjusted under 35 U.S.C. 154(b) by 227 days.

(21) Appl. No.: 15/550,499

(22) PCT Filed: Feb. 12, 2016

(86) PCT No.: PCT/GB2016/050354
§ 371 (c)(1),
(2) Date: Aug. 11, 2017

(87) PCT Pub. No.: WO2016/128773
PCT Pub. Date: Aug. 18, 2016

(65) Prior Publication Data
US 2018/0022952 A1 Jan. 25, 2018

(30) Foreign Application Priority Data
Feb. 13, 2015 (GB) .................................. 1502429.2
Jun. 19, 2015 (GB) .................................. 1510865.7

(51) Int. Cl.
| | | |
|---|---|---|
| *C09D 11/52* | (2014.01) | |
| *C09D 11/03* | (2014.01) | |
| *C07C 53/00* | (2006.01) | |
| *C07C 55/02* | (2006.01) | |
| *C07C 211/02* | (2006.01) | |
| *C07C 211/09* | (2006.01) | |
| *H01B 1/22* | (2006.01) | |
| *H01L 51/00* | (2006.01) | |
| *H05K 1/09* | (2006.01) | |
| *C08L 39/06* | (2006.01) | |
| *H01B 13/00* | (2006.01) | |

(52) U.S. Cl.
CPC .............. *C09D 11/52* (2013.01); *C07C 53/00* (2013.01); *C07C 55/02* (2013.01); *C07C 211/02* (2013.01); *C07C 211/09* (2013.01); *C08L 39/06* (2013.01); *C09D 11/03* (2013.01); *H01B 1/22* (2013.01); *H01B 13/0026* (2013.01); *H01L 51/0022* (2013.01); *H01L 51/0023* (2013.01); *H05K 1/095* (2013.01); *H05K 1/097* (2013.01); *H05K 2201/0272* (2013.01)

(58) Field of Classification Search
None
See application file for complete search history.

(56) References Cited

U.S. PATENT DOCUMENTS

| | | | | |
|---|---|---|---|---|
| 8,815,126 | B2 * | 8/2014 | Winoto ................. | B82Y 10/00 252/514 |
| 2005/0285084 | A1 | 12/2005 | Fujii et al. | |
| 2009/0140336 | A1 * | 6/2009 | Li ......................... | B82Y 10/00 257/347 |
| 2009/0148600 | A1 | 6/2009 | Li et al. | |
| 2009/0214764 | A1 * | 8/2009 | Li ......................... | B22F 1/0018 427/98.4 |
| 2010/0021704 | A1 * | 1/2010 | Yoon ..................... | H01B 1/22 428/209 |
| 2010/0037731 | A1 * | 2/2010 | Li ......................... | B22F 1/0018 75/370 |
| 2010/0084599 | A1 * | 4/2010 | Lewis ................... | B22F 1/0022 252/62.2 |
| 2011/0059234 | A1 * | 3/2011 | Byun ..................... | C23C 18/08 427/125 |
| 2013/0221288 | A1 * | 8/2013 | Liu ....................... | H01B 1/02 252/514 |
| 2013/0334470 | A1 * | 12/2013 | Kurihara ............... | B22F 1/02 252/514 |
| 2014/0004371 | A1 * | 1/2014 | Chung ................... | H01B 1/02 428/549 |
| 2014/0065387 | A1 * | 3/2014 | Andre ................... | C09D 11/03 428/209 |
| 2014/0202738 | A1 * | 7/2014 | Allemand ............. | C09D 5/24 174/251 |
| 2015/0001452 | A1 * | 1/2015 | Kurihara ............... | C09D 11/52 252/514 |

(Continued)

FOREIGN PATENT DOCUMENTS

| | | | |
|---|---|---|---|
| CN | 102220045 | A * | 10/2011 |
| CN | 102321402 | A * | 1/2012 |

(Continued)

OTHER PUBLICATIONS

English translation of JP 2009/062611, Mar. 2009; 16 pages.*
English translation of CN 102321402, Jan. 2012; 13 pages.*
English translation of CN 102220045, Oct. 2011; 10 pages.*
International Search Report and Written Opinion from related International Application No. PCT/GB2016/050354 dated Jun. 9, 2016.
Combined Search and Examination Report dated Mar. 31, 2015, issued by the UK Intellectual Property Office in connection with GB1502429.2 (7 pages).

(Continued)

*Primary Examiner* — Helene Klemanski
(74) *Attorney, Agent, or Firm* — McCarter & English, LLP

(57) ABSTRACT

A method of forming transparent electrodes using printable conductive ink containing conductive materials dispersed in a viscous liquid which upon printing and thermal treatment will vaporise fully leaving behind the conductive material only. The viscous liquid acts as a medium by which conductive material dispersions are made processable for use in various printing techniques, allowing conductive patterns to be printed onto substrates (e.g. plastics, glass, metals, ceramics).

27 Claims, No Drawings

(56) References Cited

U.S. PATENT DOCUMENTS

| | | | |
|---|---|---|---|
| 2015/0004325 A1* | 1/2015 | Walker | B05D 1/005 |
| | | | 427/469 |
| 2015/0030783 A1* | 1/2015 | Suganuma | H05K 3/106 |
| | | | 427/553 |
| 2015/0224578 A1* | 8/2015 | Okamoto | B22F 9/30 |
| | | | 252/514 |
| 2015/0225588 A1* | 8/2015 | Iguchi | B22F 9/24 |
| | | | 106/31.92 |
| 2015/0259557 A1 | 9/2015 | Sekiguchi et al. | |
| 2017/0120394 A1* | 5/2017 | Shingai | B22F 9/24 |
| 2017/0342279 A1* | 11/2017 | Kawamura | B22F 9/20 |

FOREIGN PATENT DOCUMENTS

| | | |
|---|---|---|
| EP | 2468827 A1 | 6/2012 |
| JP | 2009/062611 A * | 3/2009 |
| JP | 2015017264 A | 1/2015 |
| WO | 2009/018261 A2 | 2/2009 |
| WO | WO2010040034 A2 | 4/2010 |
| WO | WO 2013/096664 A1 * | 6/2013 |
| WO | WO 2013/105530 A1 * | 7/2013 |
| WO | WO 2014/021270 A1 * | 2/2014 |
| WO | WO 2016/093223 A1 * | 6/2016 |

OTHER PUBLICATIONS

Combined Search and Examination Report dated Nov. 20, 2015, issued by the UK Intellectual Property Office in connection with GB1510865.7 (10 pages).

* cited by examiner

CONDUCTIVE INK

CROSS-REFERENCE TO RELATED APPLICATIONS

This application is a U.S. National Phase Application under 35 U.S.C. 371 of International Application No. PCT/GB2016/050354 filed Feb. 12, 2016, which was published on Aug. 18, 2016 under International Publication Number WO 2016/128773, which claims the benefit of priority to United Kingdom Patent Application No. 1510865.7 filed Jun. 19, 2015, and United Kingdom Patent Application No. 1502429.2 filed Feb. 13, 2015. The entire contents of each of the three foregoing patent applications are incorporated herein by reference.

FIELD OF THE INVENTION

The present invention relates to a method of producing a printable conductive ink, and an ink formed by that method. The present invention further relates to a method of forming transparent printed electrodes using the conductive printable ink, and to electrodes formed by that method.

BACKGROUND OF THE INVENTION

The following discussion is not to be taken as an admission of relevant prior art.

Printable transparent conductive films are characterised by having high transparency, low sheet resistance, and stability at high current flow. Printable conductors have been used in a wide variety of optoelectronic devices (e.g. solar cells, solid state lighting, and touch screen displays). Transparent conductors are often defined as thin conductive films coated on high-transmittance surfaces or substrates. Optoelectronic devices require the electrodes to be transparent, typically using thin films of indium tin oxide (ITO) vacuum deposited onto substrates. However, the high expense, proneness to defects and fragility of ITO have led to a sharp increase in interest of alternative transparent conductors. Moreover, the process of vacuum deposition is not conducive to forming patterns and circuits, typically requiring expensive patterning processes such as photolithography. An existing method for creating patterned electrodes using vacuum deposited ITO include laser patterning, however this technique is limited by the complexity of the pattern, with more complex patterns requiring long processing times. This makes the laser patterning of ITO less economical for the production of complex transparent electrodes.

One answer to this has been to print patterns of conductive inks containing electrically conductive polymers such as poly(3,4-ethylenedioxythiophene)-poly(styrenesulfonate) (PEDOT:PSS) mixed with various polymeric additives to aid processing. However, conductive polymers are inherently coloured and possess low long-term chemical stability which are disadvantageous for application in optoelectronic devices. An alternative method is to disperse a conductive material (such as metal nanoparticles) in a solvent along with polymeric additives.

The use of a polymeric additive in the conductive ink mixture is exemplified in Chinese Patent Publication No. 2011/10444509 entitled "Preparation method of haze adjustable flexible transparent conductive film" and U.S. Pat. No. 8,815,126 entitled "Method and composition for screen printing of conductive features". These documents describe the use of a polymeric additive as an insoluble resin that acts as both a viscosity modifier to aid printability and as a binder to adhere the conductive material to a substrate. The problem with using polymeric additives is that they will also coat the conductive particles in the ink, decreasing the amount of contacts between conductive particles and increasing the percolation threshold of the mixture. To achieve similar conductivity typically requires a much larger amount of conductive material than when polymeric additives are not present, which is often prohibitively expensive and more importantly the higher loading of conductive materials decreases the transparency of the electrode. Such obstacles have thus far prevented the establishment of a permanent replacement of ITO as transparent electrode material.

Efforts to create a transparent electrode using copper nanowires can be found in, for example, U.S. Patent Publication No. 2012/0061124 to Cui et al., entitled "Electrodes and electrospun fibers". This reference discloses an electrode composed of a network of copper nanofibers having good overall flexibility, a sheet resistance of 200 $\Omega$/sq (Ohms per square) and a transmittance of around 96% for visible and near infrared (i.e., 300-1100 nanometers). This can be judged as better performance than commercial vacuum deposited ITO; however, copper nanostructured electrodes will quickly oxidize when exposed to moisture and oxygen in the atmosphere. Oxidation of the surface of the copper nanofibers will significantly degrade the electrical conductivity of these nanostructured networks. Additionally, those versed in the art will know that electrospinning of a conductive network is not suitable for the creation of patterned electrodes without several subsequent labour intensive processes. Consequently, there remains a need for a new flexible nanostructured transparent electrode design that can benefit from the advantages of using metallic nanostructures whilst also being resistant to rapid environmentally effected degeneration (e.g. reduced conductivity).

The application of conductive nanomaterials in the production of transparent electrodes has been disclosed in a number of forms, for instance, Patent Publication No. WO 2014/116738 to Allemand et al. entitled "Nanostructure transparent conductors having high thermal stability for ESD protection". This document discloses the over-coating of a protective layer onto a pre-deposited network of metallic conductive material to prevent or limit degradation of conductivity caused by environmental exposure. However, this technique limits the application of the transparent electrode by forming an insulating coating on the top surface of the electrode. Some devices require top surface conductivity to allow interaction with electrically active materials/components placed at various points on the top surface of the electrodes, such as within passively-addressed optoelectronic devices.

A number of silver-based transparent conductive films containing silver nanowires exist but they typically involve a number of complicated processing steps, for instance involving extensive silver nanowire pre-coating of a shaped "stamp" which is then used to transfer a conductive network onto the final substrate to achieve the desired electrode shape. The printing of patterns of conductive nanomaterials to produce transparent electrodes is already known, for example, US Patent Publication No. 2007/0284557 to Gruner et al., entitled "Graphene film as transparent and electrically conducting material". Such techniques as featured in this document include forming a uniform film of conductive material (e.g. graphene) by dispensing the supernatant of a graphene dispersion though a piece of filter paper and then transferring a pattern of the deposited film onto the final substrate by transfer printing using a PDMS stamp. The poor applicability of such a process would however present a number of problems for large patterns (limited by the size and ability to form a large uniform film) or different substrate materials (transferring a thin film onto a rough surface would provide significant problems) as well as expensive commercial scale production of such a labour intensive process.

SUMMARY OF THE INVENTION

According to a first aspect of the invention there is provided a method of producing a printable conductive ink, the method comprising forming a mixture of a first composition, comprising at least one amine, a second composition, comprising at least one carboxylic acid, and a conductive material. Advantageously, the combination of a first composition comprising an amine and a second composition comprising a carboxylic acid creates a viscous liquid which can act as a medium by which conductive material dispersions are made processable. Polymeric additives are required in known printable conductive inks to allow the ink to adhere to the substrate. However, such polymeric additives may drastically reduce the conductivity of a similarly printed electrode. In addition, the may increase the required concentration of conductive materials in the ink, thus increasing the required cost and reducing the transparency of the resultant electrodes. The printable conductive ink according to embodiments of the present invention is therefore advantageous compared to known printable conductive inks.

The conductive material may be mixed with the first composition prior to mixing of the second composition.

The conductive material may be mixed with the second composition prior to mixing of the first composition.

The conductive material may be added after mixing of the first and second compositions.

The at least one amine may be a primary amine or carbon-bridged diamine.

When the at least one amine is a primary amine, the at least one primary amine may have a total carbon count of 1, 2, 3, 4, or 5. Therefore, the at least one primary amine may have a total carbon count of less than 6.

When the at least one amine is a carbon-bridged diamine, the at least one carbon-bridged diamine may have a carbon count of 1, 2, 3, 4, 5, 6, 7, 8, or 9. Therefore, the at least one carbon-bridged diamine may have a carbon count less than 10.

The at least one carboxylic acid may be a carboxylic acid with a total carbon count of 1, 2, 3, 4, or 5 or a carbon-bridged dicarboxylic acid with a total carbon count of 1, 2, 3, 4, 5, 6, 7, 8, 9, 10, 11, 12, 13, 14, 15, or 16. When the at least one carboxylic acid is a carboxylic acid, it may have a total carbon count less than 6 or, when the carboxylic acid is a carbon-bridged dicarboxylic acid, it may have a total carbon count less than 17.

A mixture of carboxylic acids and amines may form the primary liquid vehicle with the required rheological properties so as to allow high resolution printing of complex electrode patterns. The mixtures of specified carboxylic acids and amines are chosen because it will allow a good range of liquids with different rheological properties to be created.

Where mixing the first and second compositions is an exothermic reaction, the method may further comprise the step of allowing the mixture to cool to form a transparent viscous liquid prior to addition of the conductive material. As stated above, the method may also comprise the dispersion of the conductive material in one or more liquid reagents prior to mixing. Advantageously, allowing the mixture to cool forms a stable transparent viscous liquid which can be stored until required. Therefore, the preliminary step in the method can be performed in advance of the step requiring the conductive ink, thus saving time and material when a set volume of ink is required.

It is preferred that the method comprises the step of mixing equimolar or substantially (e.g. +/−5% or +/−10%) equimolar quantities of amine and carboxylic acid. This is advantageous as it produces a viscous liquid that is stable at room temperature and can be stored for extended periods of time without any alteration of the rheological properties of the liquid.

In alternative embodiments the method comprises the step of mixing from 0.2 to 2 relative molar amounts of carboxylic acid with amine. The relative molar amounts of carboxylic acid may be varied to vary the viscosity of the liquid. This can be advantageous in providing a viscous liquid that works most effectively with different substrates.

It is preferred that the conductive material comprises silver nanowires. Advantageously, silver nanowires are highly conductive, making them well suited for use in an electrode printed using the conductive ink. In addition, the silver nanowires advantageously provide a high degree of tensile strength, making them beneficial to the durability of an electrode printed using the conductive ink of the present invention.

It is preferred that the silver nanowires are coated in a dispersant. Advantageously, a coating of dispersant aids formation of a stable dispersion of silver nanowires. In some embodiments, the preferred dispersant may be polyvinylpyrrolidone.

It is preferred that the present invention comprises the step of adding a polymeric additive to the mixture. While a large amount of polymeric additive may be disadvantageous, the addition of a small amount of polymeric additive to the mixture may advantageously aid printing and durability of the electrode while only slightly affecting the conductivity of the printed electrode.

According to a second aspect of the invention there is provided a method of forming printed conductive electrodes, the method comprising printing a pattern onto the surface of a substrate using conductive ink according to the method of the first aspect of the invention and heating the substrate to vaporise the conductive ink. Advantageously, the method of the second aspect provides a printed electrode produced using a printable conductive ink that includes a dispersion of conductive materials in a viscous liquid which upon heating to low/moderate temperatures (from 100° C. to 150° C.), vaporises and is completely removed from the surface of the substrate leaving behind only the conductive materials. Advantageously, the method produces a transparent electrode through the deposition of dispersible conductive materials onto a substrate using a printing method, such as screen printing, without the need to use polymeric additives to increase the viscosity of the ink. As mentioned above, use of polymeric additives in the production of printed electrodes is disadvantageous in terms of reduced conductivity of the electrode, reduced transparency, and increased cost due to the requirement of a greater concentration of conductive material to offset the reduced conductivity.

Methods of printing such as screen printing, gravure printing, flexographic printing or any other industrial printing methods known in the art may be used to print a pattern onto a surface of a substrate using the conductive ink of the first aspect of the invention. It is preferred that after printing the substrate is heated to a temperature of from 100° C. to 150° C. A temperature range of above 100° C. but below 150° C. is sufficient to vaporise the viscous liquid and leave behind only the conductive materials without damaging the substrate or the printed electrode.

It is preferred that the substrate is coated with a polymer prior to printing the electrode. Advantageously, the deposition of a uniform polymer coating onto the substrate prior to printing of the electrode increases the robustness of the electrode and aids adhesion of the conductive material to the surface of the substrate. It is further preferred that the substrate is coated with polyvinylpyrollidone. Advantageously, a coating of polyvinylpyrollidone provides a suitable surface for printing a conductive electrode.

It is preferred that pressure is applied to the printed conductive electrode. It is advantageous to apply pressure to a network of conductive particles to firstly increase the amount of contacts between neighbouring particles and secondly to increase the adhesion of the conductive network to the adhesive polymer coating on the substrate.

Alternatively, photonic sintering (for example as described in US Patent Publication No. 20150030783 entitled "Method for manufacturing transparent conductive pattern") can be used to increase neighbouring particle contacts and adhesion of the conductive network to the substrate by causing the particles to melt into the surface of the substrate. Advantageously, this reduces the need for the substrate to be coated with an adhesive polymer.

According to a third aspect of the invention there is provided a printable conductive ink produced according to the method of the first aspect of the invention. Advantageously, the printable conductive ink according to this aspect of the invention produces a viscous liquid that is stable at room temperature and requires no polymeric additives in order to be successfully printed onto a substrate. As the conductive ink overcomes the disadvantages associated with the conductivity of inks containing polymeric additives, the printable conductive ink may be used in various printing techniques to allow more complex conductive patterns to be printed onto substrates, such as plastics, glass, metals, or ceramics.

According to a fourth aspect of the invention there is provided a printed conductive electrode produced according to the method of the second aspect of the invention. Advantageously, printed conductive electrodes according to the fourth aspect of the invention do not require the presence of polymeric additives and will therefore have better conductivity. In addition, the printed conductive electrodes according to the fourth aspect of the invention are typically more cost effective due to the reduced concentration of conductive material used in the electrode.

DETAILED DESCRIPTION OF EMBODIMENTS OF THE INVENTION

Specific embodiments of the invention will further be described by way of example only.

Embodiments of the present invention relate to a simple method of producing printable conductive ink comprising a dispersion of conductive material in a viscous liquid which does not necessarily contain a polymeric additive and, also, a method of using this ink for the production of a transparent and conductive electrode pattern. In certain examples of the printable conductive ink, the rheology of the viscous liquid may be controllable to allow it to be adapted for use with a variety of printing techniques.

The absence of a polymeric additive in the conductive ink may result in the deposition of the conductive material only, a drawback of which may be low adhesion of the conductive material to the substrate, something which is provided by the polymeric additive component of typical conductive inks. The result of this, for example, may be poor robustness of the printed electrodes to any physical abrasion, hindering further over-printing or processing. One example of a technique that may be used to overcome this is the deposition of a uniform polymer coating onto the substrate before the deposition of the electrode. Deposition of a polymer on the substrate may increase the robustness of electrodes to a point where they can be processed further without easily damaging the deposited electrode and, also, without effecting the conductivity of the electrode. Addition of a polymer to the conductive ink prior to deposition may cause reduced conductivity as a result of decreased direct contact between neighbouring conductive particles brought about from the insulating layer of polymeric additive on the surface of each particle. Such insulation of the conductive materials may reduce the conductive contact between neighbouring particles and reducing the overall conductivity of the electrode.

In one embodiment of the present invention, the viscous liquid used as a medium for the conductive material may be synthesized by combining equimolar quantities of a first composition comprising an amine and a second composition comprising a carboxylic acid. These compositions may be mixed in a round-bottom flask fitted with a reflux condenser. This process can be highly exothermic and, after mixing, the product can be allowed to cool to form a viscous liquid that is stable at room temperature. The viscous liquid may be stored for extended periods of time without any alteration to the rheological properties of the liquid.

By way of example, the first composition may consist of one or more primary amines represented by formula 1, wherein, each of $R^1$ and $R^2$ is independently H or $C_{1-5}$ with a total carbon count of less than 6, or a carbon-bridged diamine represented by formula 2, wherein $R^1$ and $R^2$ consists of H or $C_{1-5}$. Also, the second composition may consist of one or more carboxylic acids represented by formula 3, wherein R consists of $C_{1-5}$ or carbon-bridged dicarboxylic acids represented by formula 4, wherein $R^1$ and $R^2$ consist of H or $C_{1-5}$.

Formula 1

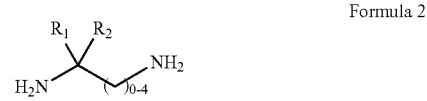

Formula 2

Formula 3

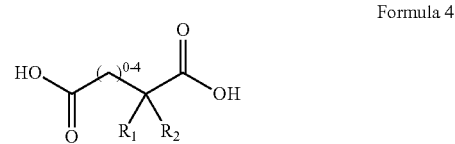

Formula 4

An exemplary method of forming the printable conductive ink and printing a transparent electrode using the ink may involve adding 0.5 moles of sec-butylamine (36.57 grams) to a two-necked round-bottom flask fitted with a reflux condenser, which has been placed in a fume-cupboard. With stirring using a magnetic stirrer bar, 0.5 moles of acetic acid (30.03 grams) can be added slowly over the course of 10 minutes by injection through a suba-seal fitted to the second neck of the flask. The reaction may be stirred for 30 minutes or until the liquid has cooled to room temperature. Once the liquid has cooled it can be decanted into a sealable container and stored until required. To make the conductive ink, silver nanowires (108 nm×30 µm) coated with PVP may be added with stirring (250 rpm) using an overhead stirrer fitted with a paddle. Silver nanowires may be added to a concentration from 5 to 15 percent of the total weight of the mixture with stirring. Following addition of the silver nanowires, the mixture may be sonicated for 30 minutes using a sonic bath. The sonicated mixture may then be stirred for a further hour at 250 rpm to ensure good dispersion. The substrate on which the electrode is to be printed may be coated with a thin film of polyvinylpyrrolidone (PVP). Once the conductive ink has been printed in the required pattern on the PVP coated substrate, the substrate may be heated in an oven fitted with an exhaust gas extractor at temperatures from 100° C. to 150° C. for from 1 to 15 minutes.

ALTERNATIVE EMBODIMENTS

Alternative embodiments which may be apparent to the skilled person on reading the above description may nevertheless fall within the scope of the invention, as defined by the accompanying claims.

The invention claimed is:

1. A method of producing a printable conductive ink, comprising:
    forming a mixture of a first composition, comprising at least one amine, wherein the at least one amine is a primary amine having a total carbon count of 1, 2, 3, 4, or 5 or wherein the at least one amine is a carbon-bridged diamine having a carbon count of 1, 2, 3, 4, 5, 6, 7, 8, or 9;
    a second composition, comprising at least one carboxylic acid, wherein the at least one carboxylic acid has a total carbon count of 1, 2, 3, 4, or 5 or wherein the at least one carboxylic acid is a carbon-bridged dicarboxylic acid with a total carbon count of 1, 2, 3, 4, 5, 6, 7, 8, 9, 10, 11, 12, 13, 14, 15, or 16; and
    a conductive material, wherein the conductive material comprises silver nanowires, wherein the silver nanowires are coated with a dispersant prior to addition of the first and second compositions.

2. The method according to claim 1, wherein the conductive material is mixed with the first composition prior to mixing of the second composition.

3. The method according to claim 1, wherein the conductive material is mixed with the second composition prior to mixing of the first composition.

4. The method according to claim 1, wherein the conductive material is mixed with the first and second compositions after mixing of the first and second compositions.

5. The method according to claim 1, wherein the at least one carboxylic acid has a total carbon count of 1, 2, 3, 4, or 5.

6. The method according to claim 1, wherein the at least one carboxylic acid has a total carbon count less than 6.

7. The method according to claim 1, wherein the at least one carboxylic acid is a carbon-bridged dicarboxylic acid with a total carbon count of 1, 2, 3, 4, 5, 6, 7, 8, 9, 10, 11, 12, 13, 14, 15, or 16.

8. The method according to claim 1, wherein the at least one carboxylic acid is a carbon-bridged dicarboxylic acid with a total carbon count less than 17.

9. The method according to claim 1, wherein mixing the first and second compositions is an exothermic reaction, the method further comprising a step of allowing the mixture to cool to form a transparent viscous liquid prior to adding the conductive material.

10. The method according to claim 1, comprising mixing equimolar quantities of amine and carboxylic acid.

11. The method according to claim 1, comprising the step of mixing from 0.2 to 2 relative molar amounts of carboxylic acid with amine.

12. The method according to claim 1, wherein the dispersant is polyvinylpyrrolidone.

13. The method according to claim 1, wherein the conductive material is added to the mixture at a concentration of from 5 to 15 weight percent relative to the total weight of mixture.

14. The method according to claim 1, wherein the conductive material is added with stirring.

15. The method according to claim 1, wherein the mixture is sonicated after addition of the conductive material.

16. The method according to claim 15, wherein the mixture is sonicated for at least 30 minutes.

17. The method according to claim 16, wherein the mixture is stirred for at least an hour following sonication.

18. The method according to claim 1, comprising the step of adding a polymeric additive to the mixture.

19. A method of forming printed conductive electrodes, comprising:
    printing a pattern onto a surface of a substrate using conductive ink produced according to claim 1, wherein the conductive ink comprises a liquid component and a conductive material component; and
    heating the substrate to vaporize the liquid component of the ink to leave the conductive material component adhered to the surface of the substrate.

20. The method according to claim 19, wherein the substrate is heated to a temperature from 100° C. to 150° C.

21. The method according to claim 19, comprising the step of coating the substrate with a polymer prior to printing the electrode.

22. The method according to claim 21, wherein the substrate is coated with polyvinylpyrrolidone.

23. The method according to claim 19, wherein pressure is applied to the printed conductive electrode.

24. The method according to claim 19, wherein photonic sintering is applied to the printed conductive electrode.

25. A printable conductive ink manufactured according to the method of claim 1.

26. A printed conductive electrode manufactured according to the method of claim 19.

27. The printed conductive electrode according to claim 26, wherein the printed conductive electrode is transparent.

* * * * *